(12) United States Patent
Sheppard et al.

(10) Patent No.: US 7,358,392 B2
(45) Date of Patent: *Apr. 15, 2008

(54) PROCESS FOR THE OXIDATIVE PURIFICATION OF TEREPHTHALIC ACID

(75) Inventors: Ronald Buford Sheppard, Kingsport, TN (US); Brent Alan Tennant, Kingsport, TN (US); Thomas Earl Woodruff, Kingsport, TN (US); Robert Lin, Kingsport, TN (US); Ruairi Seosamh O'Meadhra, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/346,393

(22) Filed: Feb. 2, 2006

(65) Prior Publication Data

US 2006/0128987 A1    Jun. 15, 2006

Related U.S. Application Data

(63) Continuation-in-part of application No. 10/645,737, filed on Aug. 21, 2003, now Pat. No. 7,074,954.

(51) Int. Cl.
C07C 51/42       (2006.01)
C07C 51/255      (2006.01)

(52) U.S. Cl. .................. 562/486; 562/416; 562/487
(58) Field of Classification Search ............ 562/416, 562/486, 487, 606
See application file for complete search history.

(56) References Cited

U.S. PATENT DOCUMENTS 3,064,044 A    11/1962   Baldwin
3,170,768 A     2/1965   Baldwin
3,513,193 A     5/1970   Katzschmann
3,584,039 A     6/1971   Meyer
3,683,018 A     8/1972   Longland, Jr.
3,839,436 A    10/1974   Longland, Jr.
3,996,271 A    12/1976   Yokota et al.
4,158,738 A  *  6/1979   Scott et al. ................. 562/416
4,201,871 A     5/1980   Tanouchi et al.
4,268,690 A     5/1981   Komatsu et al.
4,314,073 A     2/1982   Crooks (Continued)

FOREIGN PATENT DOCUMENTS

DE          3128474       6/1982

(Continued)

OTHER PUBLICATIONS

Co-pending U.S. Appl. No. 11/654,468, filed Jan. 17, 2007, Ruairi Seosamh O'Meadhra et al.

(Continued)

*Primary Examiner*—Taylor Victor Oh
(74) *Attorney, Agent, or Firm*—Steven A. Owen; Bernard J. Graves, Jr.

(57) ABSTRACT

Disclosed is a process to produce a purified carboxylic acid slurry. The process comprises removing impurities from a crystallized product in a solid liquid displacement zone to form the purified carboxylic acid slurry. The process produces purified carboxylic acid slurry having good color and low impurity levels without the use of purification steps like hydrogenation or an impurity removal process.

18 Claims, 6 Drawing Sheets

U.S. PATENT DOCUMENTS

| | | | |
|---|---|---|---|
| 4,330,676 A | 5/1982 | Moxham | |
| 4,334,086 A | 6/1982 | Hanotier et al. | |
| 4,356,319 A | 10/1982 | Roffia et al. | |
| 4,357,475 A | 11/1982 | Hanotier et al. | |
| 4,447,646 A | 5/1984 | Johnson et al. | |
| 4,605,763 A | 8/1986 | Kiefer et al. | |
| 4,707,274 A | 11/1987 | Donhauser et al. | |
| 4,812,233 A | 3/1989 | Coenen et al. | |
| 4,861,919 A | 8/1989 | Robbins et al. | |
| 4,939,297 A | 7/1990 | Browder et al. | |
| 5,008,450 A | 4/1991 | Yamamoto et al. | |
| 5,080,721 A | 1/1992 | Flanigan et al. | |
| 5,095,146 A * | 3/1992 | Zeitlin et al. | 562/486 |
| 5,107,874 A | 4/1992 | Flanigan et al. | |
| 5,116,423 A | 5/1992 | Kokkonen et al. | |
| 5,143,554 A | 9/1992 | Koyama et al. | |
| 5,200,557 A | 4/1993 | Gee et al. | |
| 5,359,133 A | 10/1994 | Nazimok et al. | |
| 5,454,959 A | 10/1995 | Stevens | |
| 5,527,957 A | 6/1996 | Hindmarsh et al. | |
| 5,563,293 A | 10/1996 | Hindmarsh et al. | |
| 5,583,254 A | 12/1996 | Turner et al. | |
| 5,616,792 A | 4/1997 | Bartos et al. | |
| 5,635,074 A | 6/1997 | Stenstrom et al. | |
| 5,643,468 A | 7/1997 | Ure | |
| 5,676,847 A | 10/1997 | Yamamoto et al. | |
| 5,679,846 A | 10/1997 | Hindmarsh et al. | |
| 5,684,187 A | 11/1997 | Ohkoshi et al. | |
| 5,698,734 A | 12/1997 | Turner et al. | |
| 5,712,412 A | 1/1998 | Inary et al. | |
| 5,777,161 A | 7/1998 | Inary | |
| 5,840,965 A | 11/1998 | Turner et al. | |
| 5,840,968 A | 11/1998 | Lee et al. | |
| 5,925,786 A | 7/1999 | Isayama et al. | |
| 5,955,394 A | 9/1999 | Kelly | |
| 6,228,215 B1 | 5/2001 | Hoffman, Jr. | |
| 6,495,044 B1 | 12/2002 | Verdoes | |
| 6,517,733 B1 | 2/2003 | Carlson | |
| 6,797,073 B1 | 9/2004 | Teruggi et al. | |
| 2003/0004372 A1 | 1/2003 | Piras et al. | |
| 2004/0215036 A1 | 10/2004 | Lin et al. | |
| 2004/0245176 A1 | 12/2004 | Parker et al. | |
| 2004/0260052 A1 | 12/2004 | Nagao et al. | |
| 2005/0087215 A1 | 4/2005 | Miyahara et al. | |

FOREIGN PATENT DOCUMENTS

| | | |
|---|---|---|
| GB | 983677 | 2/1965 |
| GB | 1152577 | 5/1969 |
| GB | 1260755 | 1/1972 |
| GB | 1358520 | 7/1974 |
| GB | 1388289 | 3/1975 |
| JP | 48-26740 | 9/1973 |
| JP | 7-149690 | 6/1995 |
| JP | 7-291896 | 11/1995 |
| JP | 9-286758 | 11/1997 |
| JP | 9-286759 | 11/1997 |
| JP | 2001-139514 | 5/2001 |
| JP | 2001-247511 | 9/2001 |
| JP | 2001-288139 | 10/2001 |
| JP | 2002-230819 | 8/2002 |
| WO | WO 93/24440 | 12/1993 |
| WO | WO 94/17892 | 8/1994 |
| WO | WO 2004/052820 A1 | 6/2004 |
| WO | WO 2006/125144 A1 | 11/2006 |

OTHER PUBLICATIONS

USPTO Office Action dated May 1, 2007 for copending U.S. Appl. No. 10/758,676.

USPTO Office Action dated Oct. 4, 2005 for U.S. Appl. No. 10/667,744.

USPTO Office Action dated Jul. 12, 2005 for U.S. Appl. No. 10/667,744.

USPTO Office Action dated Nov. 29, 2004 for U.S. Appl. No. 10/667,744.

USPTO Office Action dated Nov. 30, 2004 for U.S. Appl. No. 10/645,734.

USPTO Office Action dated Apr. 21, 2004 for U.S. Appl. No. 10/645,734.

USPTO Office Action dated Apr. 22, 2003 for U.S. Appl. No. 10/315,294.

USPTO Office Action dated Dec. 10, 2004 for U.S. Appl. No. 10/645,737.

USPTO Office Action dated Apr. 19, 2004 for U.S. Appl. No. 10/645,737.

Copending U.S. Appl. No. 10/315,295, filed Dec. 9, 2002.
Copending U.S. Appl. No. 10/315,294, filed Dec. 9, 2002.
Copending U.S. Appl. No. 10/645,737, filed Aug. 21, 2003.
Copending U.S. Appl. No. 10/645,734, filed Aug. 21, 2003.
Copending U.S. Appl. No. 10/667,744, filed Sep. 22, 2003.
Copending U.S. Appl. No. 10/872,248, filed Jun. 18, 2004.
Copending U.S. Appl. No. 10/758,676, filed Jan. 15, 2004.

USPTO office action dated Aug. 2, 2006 for copending U.S. Appl. No. 10/758,676.

USPTO office action dated Aug. 24, 2006 for copending U.S. Appl. No. 10/872,248.

USPTO Office Action dated Jul. 13, 2007 for co-pending U.S. Appl. No. 10/872,248.

USPTO Office Action dated Jan. 9, 2008 for copending U.S. Appl. No. 10/758,676.

USPTO Office Action dated Sep. 21, 2007 for copending U.S. Appl. No. 10/872,248.

* cited by examiner

| | TEMPERATURE | | | | |
|---|---|---|---|---|---|
| | 160 | 160 | | 170 | 170 |
| TIME | 4-CBA | p-TA | TIME | 4-CBA | p-TA |
| 0.00 | 1098.3 | 1486.3 | 0.00 | 1098.3 | 1486.3 |
| 0.15 | 1226.7 | 1332.5 | 0.08 | 1464.7 | 1199.2 |
| 1.27 | 1120.1 | 1260.4 | 0.52 | 1519.4 | 1079.9 |
| 1.65 | 1000.8 | 1042.7 | 1.08 | 1412.6 | 1236.6 |
| 2.18 | 898.5 | 774.5 | 1.60 | 1129.0 | 957.0 |
| 2.67 | 791.0 | 507.9 | 2.08 | 976.2 | 708.7 |
| 3.15 | 667.2 | 257.5 | 2.67 | 765.7 | 545.0 |
| 3.62 | 599.1 | 181.4 | 3.27 | 703.3 | 334.3 |
| 4.13 | 620.4 | 136.7 | 3.60 | 483.4 | 161.6 |
| 4.63 | 225.8 | 161.3 | 4.13 | 593.2 | 229.4 |

*Table 2A*

ANALYSIS OF SLURRY SAMPLES

| | TEMPERATURE | | | | | |
|---|---|---|---|---|---|---|
| | 190 | 190 | | 200 | 200 | |
| TIME | 4–CBA | p–TA | TIME | 4–CBA | p–TA | |
| 0.00 | 1173.0 | 1455.2 | 0.00 | 1180.6 | 1426.2 | |
| 0.12 | 1536.8 | 1030.2 | 0.02 | 1182.9 | 1250.3 | |
| 0.58 | 1082.2 | 1313.3 | 0.42 | 1180.0 | 1550.6 | |
| 1.13 | 1103.9 | 1308.4 | 0.83 | 898.6 | 1207.2 | |
| 1.65 | 927.5 | 1153.4 | 1.25 | 680.9 | 956.5 | |
| 2.07 | 766.7 | 878.3 | 1.75 | 419.4 | 347.6 | |
| 3.12 | 379.1 | 315.0 | 2.55 | 152.8 | 0.0 | |
| 4.05 | 291.5 | 55.9 | 3.60 | 103.9 | 0.0 | |
| 5.48 | 278.8 | 29.1 | 4.50 | 128.3 | 0.0 | |
| 6.32 | 123.5 | 0.0 | 5.30 | 156.6 | 0.0 | |

*Table 2B*

ANALYSIS OF SLURRY SAMPLES

| | TEMPERATURE | | | | | |
|---|---|---|---|---|---|---|
| | 160 | 160 | | 170 | 170 | |
| TIME | 4-CBA | p-TA | TIME | 4-CBA | p-TA | |
| 0.00 | 2507.6 | 433.0 | 0.00 | 2507.6 | 433.0 | |
| 0.07 | 2476.1 | 798.0 | 0.02 | 2239.9 | 668.4 | |
| 1.12 | 2239.3 | 681.2 | 0.52 | 2278.5 | 636.1 | |
| 1.65 | | | 1.00 | 2197.3 | 636.2 | |
| 2.08 | 2221.1 | 537.0 | 1.52 | 2132.4 | 585.6 | |
| 2.58 | 2100.7 | 286.0 | 2.03 | 1931.7 | 435.4 | |
| 3.08 | 1874.4 | 205.7 | 2.58 | 1819.3 | 393.3 | |
| 3.55 | 1814.4 | 162.3 | 3.13 | 1634.0 | 244.3 | |
| 4.07 | 1679.2 | 142.1 | 3.53 | 1641.2 | 199.1 | |
| 4.57 | 1726.2 | 129.1 | 4.02 | 1595.3 | 161.5 | |

*Table 3A*

ANALYSIS OF SOLID SAMPLES

| | TEMPERATURE | | | | | |
|---|---|---|---|---|---|---|
| | 190 | 190 | | 200 | 200 | |
| TIME | 4-CBA | p-TA | TIME | 4-CBA | | p-TA |
| 0.00 | 2254.2 | 726.7 | 0.00 | 2254.2 | | 726.7 |
| 0.12 | 2291.5 | 729.7 | 0.02 | 2224.8 | | |
| 0.58 | 2064.3 | 744.4 | 0.42 | 1721.6 | | |
| 1.13 | 1835.7 | 594.8 | 0.83 | 2171.5 | | |
| 1.65 | 1531.9 | 539.4 | 1.25 | 1431.3 | | |
| 2.07 | 1419.5 | 227.4 | 1.75 | 2399.8 | | 863.5 |
| 3.12 | 1168.1 | 75.8 | 2.55 | 873.4 | | |
| 4.05 | 1042.2 | 54.0 | 3.60 | 699.5 | | |
| 5.48 | 1103.9 | 70.3 | 4.50 | | | |
| 6.32 | 1157.2 | 96.6 | 5.30 | 663.7 | | |

*Table 3B*

ANALYSIS OF SOLID SAMPLES

PROCESS FOR THE OXIDATIVE PURIFICATION OF TEREPHTHALIC ACID

CROSS-REFERENCE TO RELATED APPLICATIONS

This application is a continuation-in-part of U.S. application Ser. No. 10/645,737, filed Aug. 21, 2003, now U.S. Pat. No. 7,074,954 hereby incorporated by reference in its entirety.

FIELD OF INVENTION

The present invention relates to a process for the purification of a crude carboxylic acid slurry. More specifically, the present invention relates to a process comprising the steps of displacing at elevated temperatures, mother liquor from a crystallized product and reslurrying the crystallized product to be separated in a solid liquid displacement zone to form a purified carboxylic acid slurry.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities present due to the oxidation of para-xylene. Typical commercial process produce a crude terephthalic acid then dissolve the solid crude terephthalic acid in water at high temperatures and pressures, hydrogenating the resultant solution, cooling and crystallizing the terephthalic acid product out of solution, and separating the solid terephthalic product from the liquid as discussed in U.S. Pat. No. 3,584,039 herein incorporated by reference.

In many processes colored impurities from the benzil, and fluorenone families are hydrogenated to colorless products and leave the process with the terephthalic acid solid product and wastewater streams. However, this invention provides an attractive process to produce a purified carboxylic acid slurry by utilizing a solid liquid displacement zone comprising a solid liquid separator at elevated temperatures after oxidation of a crude carboxylic acid slurry product and prior to final filtration and drying.

SUMMARY OF THE INVENTION

In one embodiment of the invention, a process to produce the purified carboxylic acid slurry is provided without the use of hydrogenation of the terephthalic acid or a process separating impurities from oxidation solvent as disclosed in U.S. Pat. No. 3,584,039. Another example of a process for separating impurities from oxidation solvent is U.S. Pat. No. 4,356,319.

In another embodiment of this invention, a process to produce a purified carboxylic acid slurry, the process comprising removing impurities from a crystallized product in a solid liquid displacement zone to form the purified carboxylic acid slurry; wherein the purified carboxylic acid slurry has a b* of less than 3.5; wherein the purified carboxylic acid slurry is formed without a hydrogenation step.

In another embodiment of this invention, a process to purify a staged oxidation product the process comprising removing impurities from the staged oxidation product in a solid liquid displacement zone to form a purified staged oxidation product; wherein the purified staged oxidation product has a b* of less than 3.5; wherein the purified staged oxidation product is formed without a hydrogenation step.

In another embodiment of this invention, a process to produce a purified carboxylic acid slurry is provided. The process comprises removing in a solid liquid displacement zone impurities from a crystallized product to form the purified carboxylic acid slurry; wherein the solid liquid displacement zone comprises a solid liquid separator that is operated at a temperature between about 140° C. to about 160° C.; wherein the solid liquid separator is operated in a continuous mode; and wherein the solid liquid separator is operated at a pressure of less than about 70 psia.

In another embodiment of this invention, a process to produce a purified carboxylic acid slurry is provided. The process comprising:

(a) optionally, removing impurities from a crude carboxylic acid slurry in an optional solid liquid displacement zone to form a slurry product;

(b) oxidizing the slurry product or the crude carboxylic acid slurry in a staged oxidation zone to form a staged oxidation product;

(c) crystallizing the staged oxidation product in a crystallization zone to form a crystallized product; and (d) removing in a second solid liquid displacement zone impurities from the crystallized product to form the purified carboxylic acid slurry.

In yet another embodiment of this invention, a process to produce a purified carboxylic acid slurry is provided. The process comprises:

(a) optionally, removing impurities from a crude carboxylic acid slurry in an optional solid liquid displacement zone to form a slurry product;

(b) oxidizing the slurry product or the crude carboxylic acid slurry in a staged oxidation zone to form a staged oxidation product;

(c) removing in a solid liquid displacement zone impurities from the staged oxidation product to form a purified staged oxidation product; and (d) crystallizing the purified staged oxidation product in a crystallization zone to form the purified carboxylic acid product.

These objects, and other objects, will become more apparent to others with ordinary skill in the art after reading this disclosure.

DETAILED DESCRIPTION OF THE INVENTION

The present invention provides a process for the purification of a crude carboxylic acid slurry. The process comprises the steps of displacing at elevated temperatures mother liquor from a crystallized product and reslurrying the crystallized product in a solid liquid displacement zone to form a purified carboxylic acid slurry.

Crude terephthalic acid is conventionally made via the liquid phase air oxidation of paraxylene in the presence of a suitable oxidation catalyst. Suitable catalysts comprises at least one selected from, but are not limited to, cobalt, bromine and manganese compounds, which are soluble in the selected solvent. Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 8:1 and about 20:1. Throughout the specification acetic acid will be referred to as the solvent. However, it should be appreciated that other suitable solvents, such as those disclosed herein, may also be utilized. Patents disclosing the production of terephthalic acid such as U.S. Pat. Nos. 4,158,738 and 3,996,271 are hereby incorporated by reference.

Figure 1:
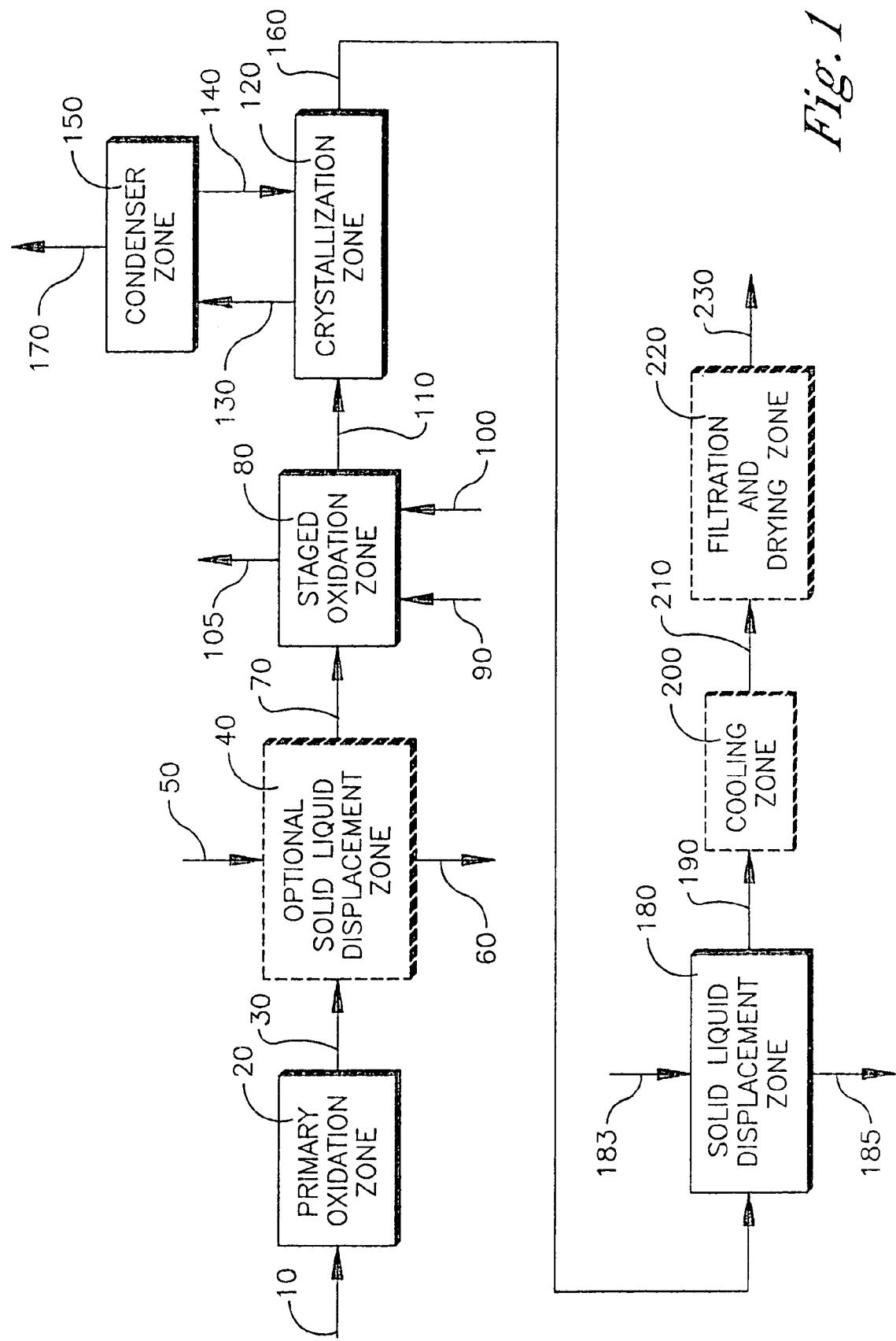
FIG. 1 is a schematic of the inventive process for the oxidative purification of carboxylic acid wherein a liquid displacement zone is utilized after the crystallization zone.

In an embodiment of this invention a process to produce purified carboxylic acid slurry 190 is provided in FIG. 1. The process comprises removing impurities from a crystallized product in a solid liquid displacement zone 180 to form the purified carboxylic acid slurry 190; wherein the purified carboxylic acid slurry 190 has a b* of less than 3.5; wherein the purified carboxylic acid slurry 190 is formed without a hydrogenation step.

The solid liquid separation zone 180, impurities, crystallized product 160, and purified carboxylic acid slurry 190 are all described subsequently in this disclosure.

In another embodiment of this invention, a process to purify a staged oxidation product 110 the process comprising removing impurities from the staged oxidation product 110 in a solid liquid displacement zone 180 to form a purified staged oxidation product 165; wherein the purified staged oxidation product 165 has a b* of less than 3.5; wherein the purified staged oxidation product 165 is formed without a hydrogenation step.

The solid liquid separation zone 180, impurities, staged oxidation product 110, and the purified staged oxidation product 165 are all described subsequently in this disclosure.

In another embodiment of this invention a process to produce a purified terephthalic acid slurry 190 is provided in FIG. 1. The process comprises:

Step (a) comprises optionally removing impurities from a crude carboxylic acid slurry 30 in an optional solid liquid displacement zone 40 to form a slurry product 70;

A crude carboxylic acid slurry 30 comprises at least one carboxylic acid, catalyst, at least one solvent, and impurities is withdrawn via line 30 can be at temperatures between about 110° C. and about 200° C., preferably about 140° C. to about 170° C. from the a primary oxidation zone 20 wherein an aromatic feedstock 10, typically paraxylene is oxidized. The impurities typically comprise one or more of the following compounds: 4-carboxybenzaldehyde, trimellitic acid, and 2,6-dicarboxyfluorenone. The solvent typically comprises acetic acid, but can be any solvent that has been previously mentioned.

Generally, the crude carboxylic acid slurry 30 is produced by oxidizing in a primary oxidation zone 20 an aromatic feed stock 10. In one embodiment, the aromatic feedstock comprises paraxylene. The primary oxidation zone 20 comprises at least one oxidation reactor, and the crude carboxylic acid slurry 30 comprises at least one carboxylic acid. Generally, the carboxylic acid is terephthalic acid.

Therefore, when terephthalic acid is utilized, the crude carboxylic acid slurry 30 would be referred to as crude terephthalic acid slurry. However, suitable carboxylic acids include, but are not limited to, terephthalic acid, isophthalic acid, naphthalene dicarboxylic acid, and mixtures thereof. Crude terephthalic acid slurry is conventionally synthesized via the liquid phase oxidation of paraxylene in the presence of suitable oxidation catalyst. Suitable catalysts include, but are not limited to, cobalt, manganese and bromine compounds, which are soluble in the selected solvent.

The crude carboxylic acid slurry in conduit 30 is fed to an optional solid liquid displacement zone 40 capable of removing a portion of the liquid contained in the crude carboxylic acid slurry 30 to produce the slurry product in conduit 70. The removal of a portion of the liquid to produce a slurry product in conduit 70 can be accomplished by any means known in the art. Typically, the solid liquid displacement zone 40 comprises a solid liquid separator that is selected from the group consisting of a decanter centrifuge, rotary disk centrifuge, belt filter, rotary vacuum filter, and the like. The crude carboxylic acid slurry in conduit 30 is fed to the optional solid liquid displacement zone 40 comprising a solid liquid separator. The solid liquid separator is operated at temperatures between about 50° C. to about 200° C., preferably 140° C. to about 170° C. and at pressures between about 30 psig to about 200 psig. The residence time can be any residence time suitable to remove a portion of the solvent and produce a slurry product in conduit 70. The optional solid liquid separator in the optional solid liquid displacement zone 40 may be operated in continuous or batch mode, although it will be appreciated that for commercial processes, the continuous mode is preferred.

The impurities are displaced from the optional solid liquid displacement zone 40 in a mother liquor and withdrawn via line 60. Additional solvent is fed to the optional solid liquid displacement zone 40 via line 50 to reslurry the crude carboxylic acid slurry 30 and form a slurry product 70. The mother liquor is withdrawn from solid liquid displacement zone 40 via line 60 and comprises a solvent, typically acetic acid, catalyst, and bromine compounds. The mother liquor in line 60 may either be sent to a process for separating impurities from oxidation solvent from via lines not shown or recycled to the catalyst system via lines not shown. One technique for impurity removal from the mother liquor commonly used in the chemical processing industry is to draw out or "purge" some portion of the recycle stream. Typically, the purge stream is simply disposed of or, if economically justified, subjected to various treatments to remove undesired impurities while recovering valuable components. Examples of impurity removal processes include U.S. Pat. Nos. 4,939,297 and 4,356,319, herein incorporated by reference.

Step (b) comprises oxidizing the slurry product 70 or crude carboxylic acid slurry 30 in a staged oxidation zone 80 to form a staged oxidation product 110.

In one embodiment of the invention the slurry product 70 or crude carboxylic acid slurry 30 is withdrawn via line 70 to a staged oxidation zone 80 where it can be heated to between about 150° C. to about 280° C., or about 160° C. to about 280° C., or about 150° C. to about 180° C., or about 160° C. to about 180° C., or about 190° C. to about 280° C., another range is about 200° C. to about 250° C. and yet other ranges are about 170° C. to about 200° C., or about 180° C. to about 220° C. and further oxidized with air fed by line 100 to produce a staged oxidation product 110.

The staged oxidation zone 80 comprises at least one staged oxidation reactor vessel. The crude carboxylic acid slurry 30 or slurry product 70 is fed to the staged oxidation zone 80. The term "staged" means that the oxidation occurs in both the primary oxidation zone 20 discussed previously as well as in the staged oxidation zone 80. For example, the staged oxidation zone 80 can comprise staged oxidation reactor vessels in series.

When the carboxylic acid is terephthalic acid, the crude carboxylic acid slurry 30 or slurry product 70 in the staged oxidation zone 80 comprises an oxidation reactor that is heated to between about 190° C. to about 280° C., preferably between about 200° C. to about 250° C., and most preferably between 205° C. to 225° C. and further oxidized with air or a source of molecular oxygen fed by line 100 to produce a staged oxidation product 110. Generally, oxidation in the staged oxidation zone 80 is at a higher temperature than the oxidation in the primary oxidation zone 20 to enhance the impurity removal. The staged oxidation zone 80 can be heated directly with solvent vapor, or steam via conduit 90 or indirectly by any means known in the art. The staged oxidation zone 80 is operated at a temperature and pressure sufficient that the b* color of the staged oxidation product 110 is less than about 4. Preferably, the b* color of the staged oxidation product in conduit 110 is less than about 3.5. Most preferably, the b* color in the staged oxidation product in conduit 110 is less than about 3. The b* color is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

Additional air or molecular oxygen may be fed via conduit 100 to the staged oxidation zone 80 in an amount necessary to oxidize a substantial portion of the partially oxidized products such as 4-carboxybenzaldehyde (4-CBA) in the crude carboxylic acid slurry 30 or slurry product 70 to the corresponding carboxylic acid. Generally, at least 70% by weight of the 4-CBA is converted to terephthalic acid in the staged oxidation zone 80. Preferably, at least 80% by weight of the 4-CBA is converted to terephthalic acid in the staged oxidation zone 80. Significant concentrations of 4-carboxybenzaldehyde and p-toluic acid in the terephthalic acid product are particularly detrimental to polymerization processes as they act as a chain terminator during the condensation reaction between terephthalic acid and ethylene glycol in the production of polyethylene terephthalate (PET). Typical terephthalic acid product contains on a weight basis less than about 250 parts per million (ppm) 4-carboxybenzaldehyde and less than about 150 ppm p-toluic acid Impurities in the crude carboxylic acid slurry 30 or slurry product 70 go into solution as terephthalic acid particles are dissolved and re-crystallized in staged oxidation zone, 80. Offgas from the staged oxidation zone 80 is withdrawn via line 105 and fed to a recovery system where the solvent is removed from the offgas comprising volatile organic compounds (VOCs). VOCs and methyl bromide may be treated, for example by incineration in a catalytic oxidation unit. The staged oxidation product 110 from the staged oxidation zone 80 is withdrawn via line 110.

Step (c) comprises crystallizing the staged oxidation product 110 in a crystallization zone 120 to form a crystallized product 160. Generally, the crystallization zone 120 comprises at least one crystallizer. Vapor product from the crystallization zone 120 is withdrawn via line 130, condensed in a condenser zone 150, which comprises at least one condenser and returned to the crystallization zone 120 via conduit 140. Optionally, the liquid in conduit 140 or vapor 130 in the condenser zone 150 can be recycled, or it can be withdrawn or sent to an energy recovery device. In addition, the crystallization offgas 170 from the condenser zone 150 is removed via line 170 and can be routed to a recovery system where the solvent is removed and crystallization offgas comprising VOCs and pollutants may be treated, for example by incineration in a catalytic oxidation unit.

When the carboxylic acid is terephthalic acid, the staged oxidation product 110 from the staged oxidation zone 80 is withdrawn via line 110 and fed to a crystallization zone 120 comprising at least one crystallizer where it is cooled to a temperature between about 110° C. to about 190° C. to form a crystallized product 160, preferably to a temperature between about 140° C. to about 180° C., most preferably 150° C. to 170° C. The b* color of the crystallized product in conduit 160 is less than 4. Preferably, the b* color of the crystallized product in conduit 160 is less than 3.5. Most preferably, the b* color in the crystallized product in conduit 160 is less than 3.

The crystallized product 160 from the crystallization zone 120 is withdrawn via line 160. Typically, the crystallized product 160 is then fed directly to a vessel and cooled to form a cooled crystallized product. When the carboxylic acid is terephthalic acid, the cooled crystallized product is cooled in a vessel to typically a temperature of approximately 90° C. or less before being introduced into a process for recovering the terephthalic acid as a dry powder or wet cake.

In some processes prior to the present invention, the crystallized product 160 was fed directly to a flash tank. The crystallized product 160 was cooled in the flash tank to typically less than about 90° C. and fed to a filtration and drying system. However, as previously stated this invention provides an attractive process to produce a purified carboxylic acid slurry by utilizing a solid liquid displacement zone comprising a solid liquid separator at elevated temperatures after oxidation of a crude carboxylic acid slurry product and prior to final filtration and drying. The results of Examples 1 and 2 discussed subsequently clearly illustrate the significant purity improvements which are achieved when the solid liquid displacement zone of the present invention is used.

Step (d) comprises removing in a solid liquid displacement zone 180 impurities from the crystallized product to form the purified terephthalic acid slurry.

It has been surprisingly found that when the crystallized product 160 from crystallizer zone 120 is treated in a solid liquid displacement zone 180, the purified carboxylic acid slurry 190 contains significantly less impurities, thereby improving the color of the products produced from the carboxylic acid. The solid liquid displacement zone 180 comprises a solid liquid separator which includes, but is not limited to a decanter centrifuge, rotary disk pack centrifuge and other suitable solid liquid separation devices. In the embodiment where the carboxylic acid is terephthalic acid, the level of impurities in the purified carboxylic acid slurry is decreased by up to 60%. It was completely unexpected that terephthalic acid of this purity could be produced utilizing the second solid liquid displacement zone 180 of the present invention without the use of a process for separating impurities from oxidation solvent as disclosed in U.S. Pat. No. 4,939,297 or hydrogenation as disclosed in U.S. Pat. No. 3,584,039; both of which are herein incorporated by reference.

Thus, in one embodiment of the present invention, the crystallized product 160 is withdrawn from crystallizer zone 120 via line 160 and is fed to a solid liquid displacement zone 180 comprising a solid liquid separator to produce a purified carboxylic acid slurry in conduit 190. The solid liquid displacement zone 180 comprises a solid liquid separator. In one embodiment of the invention the solid liquid separator can be operated at temperatures between about 50°

C. to about 200° C., another range is the solid liquid separator can be operated at 110° C. to 200° C., preferably between about 120° C. to about 180° C., and more preferably between about 140° C. to about 160° C. and at pressures above the flash point for the selected solvent. For the case where the solvent is acetic acid, the pressure is generally less than 200 psia. The solid liquid separator in the second solid liquid displacement zone 180 may be operated in continuous or batch mode, although it will be appreciated that for commercial processes the continuous mode is preferred.

The impurities are displaced from the solid liquid displacement zone 180 in a mother liquor stream and withdrawn via line 185. Additional solvent is fed to the solid liquid displacement zone 180 via line 183 to reslurry the crystallized product and form the purified terephthalic acid slurry. The purified carboxylic acid slurry is withdrawn from displacement zone 180, via line 190. Optionally, the purified carboxylic acid slurry in conduit 190 can then be fed to a flash tank and flash cooled to less than about 90° C.

Figure 2:
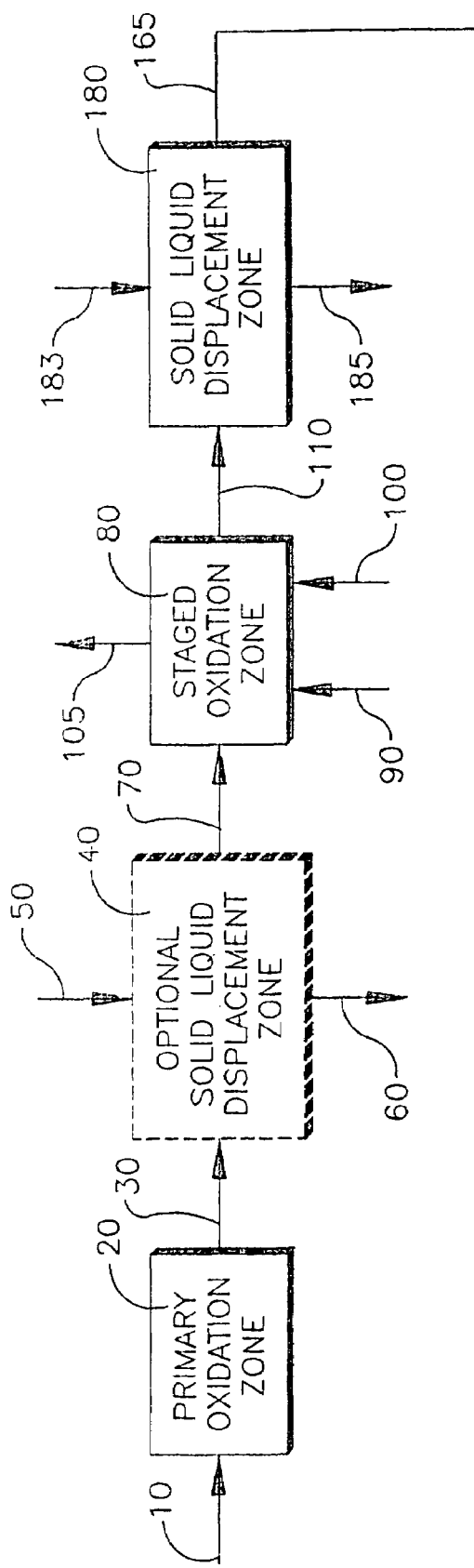
FIG. 2 is a schematic of the inventive process for the oxidative purification of carboxylic acid wherein a liquid displacement zone is utilized after the staged oxidation zone.
Figure 2:
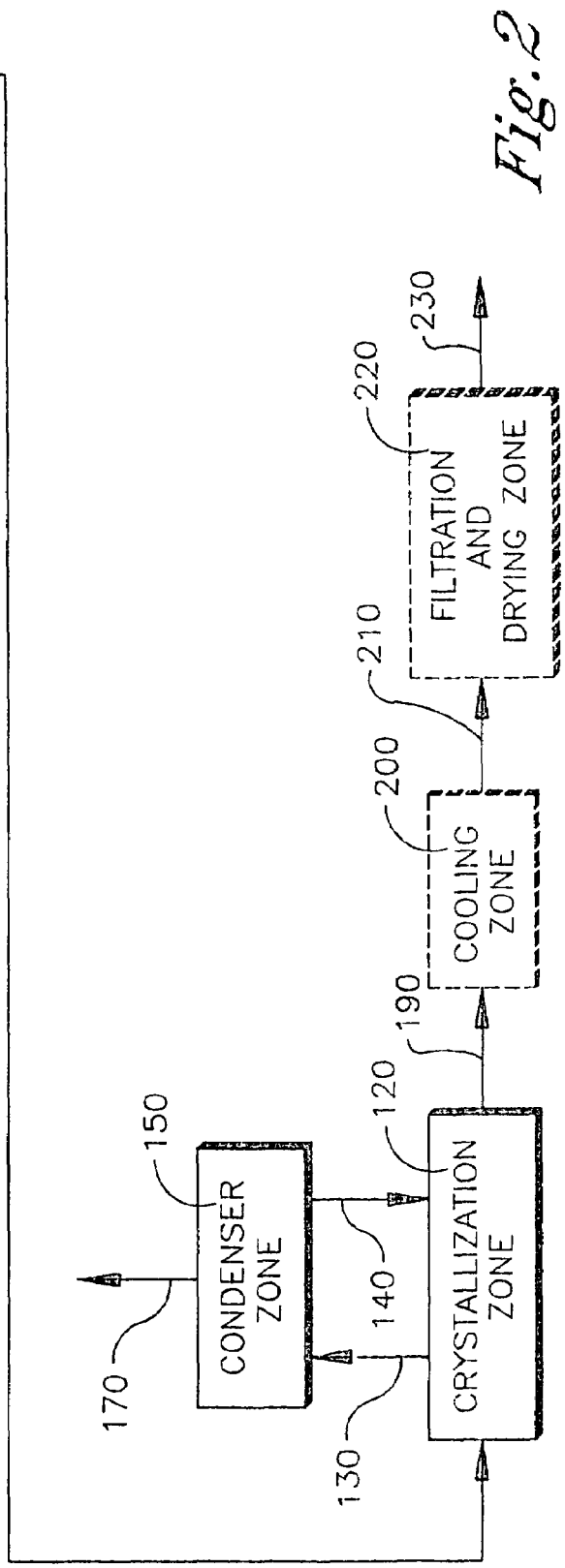

In other embodiments of this invention, the solid liquid displacement zone 180 can be located after the staged oxidation zone 80 as shown in FIG. 2. Even though the process zones are located in a different order, the function of the zones are the same as previously described. Impurities are displaced from the feed stream from the solid liquid displacement zone 180 via line 185. The feed stream to the solid displacement zone 180 is the staged oxidation product 110. When the feed stream to the solid liquid displacement zone 180 is a staged oxidation product 110 a purified staged oxidation product 165 is produced. The impurities are displaced from the solid liquid displacement zone 180 in a mother liquor stream and withdrawn via line 185.

The mother liquor stream 185 comprises carboxylic acid, water, a solvent, suitable oxidation catalyst(s) and bromine compounds and corrosion metals. The bromine compounds are used as promoters in the oxidation reaction. Examples of corrosion metals are iron and chromium compounds, which inhibit, reduce or entirely destroy the activity of the suitable oxidation catalyst. Suitable carboxylic acids are selected from the group consisting of terephthalic acid, isophthalic acid, naphthalene dicarboxylic acid, and mixtures thereof. Additional solvent is fed to the solid liquid displacement zone 180 via line 183 to reslurry the crystallized product and form the purified terephthalic acid slurry. The purified carboxylic acid slurry is withdrawn from the solid liquid displacement zone 180, via line 190. Optionally, the purified carboxylic acid slurry in conduit 190 can then be fed to a flash tank and flashed cooled to less than about 90° C.

Step (e) comprises optionally cooling the purified carboxylic acid slurry in a cooling zone 200 to form a cooled purified carboxylic acid slurry 210.

The purified carboxylic acid slurry 190 is withdrawn from solid liquid displacement zone 180 via line 190. The purified carboxylic acid slurry 190 is fed to a cooling zone 200 and cooled to less than about 90° C. The cooling of the purified carboxylic acid slurry can be accomplished by any means known in the art, typically the cooling zone 200 comprises a flash tank.

Step (f) comprises optionally filtering and drying the cooled purified carboxylic slurry 210 or the purified carboxylic acid slurry in a filtration and drying zone 220 to remove a portion of the solvent from the cooled carboxylic acid slurry 210 to produce the purified carboxylic acid product 230.

The cooled, purified carboxylic acid slurry 190 is withdrawn from cooling zone 200 and fed to a filtration and drying zone 220. A portion of the solvent and remaining catalyst and impurities is separated, and the purified carboxylic acid product is withdrawn via line 230.

The filtration and drying zone 220 comprises a filter suitable for recovering the solid carboxylic acid and a dryer. The filtration can be accomplished by any means known in the art. For example, a rotary vacuum filter can be used for the filtration to produce a filtration cake. The filtration cake goes through an initial dewatering step, is then rinsed with acid wash to remove residual catalyst, and can be dewatered again before sent to the dryers. The drying of the filter cake can be accomplished by any means known in the art that's capable of evaporating at least 10% of the volatiles remaining in the filter cake to produce the carboxylic acid product. For example, a Single Shaft Porcupine® Processor dryer can be used.

In other embodiments of this invention, the solid liquid displacement zone 180 can be located after the staged oxidation zone 80 as shown in FIG. 2. Even though the process zones are located in a different order, the function of the zones are the same as previously described. Impurities are displaced from the feed stream from the solid liquid displacement zone 180 via line 185. The feed stream to the solid displacement zone 180 is the staged oxidation product 110. When the feed stream to the solid liquid displacement zone 180 is a staged oxidation product 110 a purified staged oxidation product 165 is produced. The impurities are displaced from the solid liquid displacement zone 180 in a mother liquor stream and withdrawn via line 185.

The mother liquor stream 185 comprises carboxylic acid, water, a solvent, suitable oxidation catalyst(s) and bromine compounds and corrosion metals. The bromine compounds are used as promoters in the oxidation reaction. Examples of corrosion metals are iron and chromium compounds, which inhibit, reduce or entirely destroy the activity of the suitable oxidation catalyst. Suitable carboxylic acids are selected from the group consisting of terephthalic acid, isophthalic acid, naphthalene dicarboxylic acid, and mixtures thereof. Additional solvent is fed to the solid liquid displacement zone 180 via line 183 to reslurry the crystallized product and form the purified terephthalic acid slurry. The purified carboxylic acid slurry is withdrawn from the solid liquid displacement zone 180, via line 190. Optionally, the purified carboxylic acid slurry in conduit 190 can then be fed to a flash tank and flash cooled to less than about 90° C.

It should be appreciated that the process zones previously described can be utilized in any other logical order. It should also be appreciated that when the process zones are reordered that the process conditions may change.

In another embodiment of this invention each embodiment can optionally include an additional step comprising decolorizing the carboxylic acid or an esterified carboxylic acid via hydrotreatment.

The decolorizing of the purified carboxylic acid slurry or an esterified carboxylic acid can be accomplished by any means known in the art and is not limited to hydrogenation. However, for example in one embodiment of the invention, the decolorizing can be accomplished by reacting a carboxylic acid that has undergone esterification treatment, for example with ethylene glycol, with molecular hydrogen in the presence of a catalyst in a reactor zone to produce a decolorized carboxylic acid solution or a decolorized ester product. For the reactor zone, there are no special limitations in the form or construction thereof, subject to an arrangement that allows supply of hydrogen to effect intimate contact of the carboxylic acid or ester product with the catalyst in the reactor zone. Typically, the catalyst is usually a single Group VIII metal or combination of Group VIII metals. Preferably, the catalyst is selected from a group consisting of palladium, ruthenium, rhodium and combination thereof. The reactor zone comprises a hydrogenation reactor that operates at a temperature and pressure sufficient to hydrogenate a portion of the characteristically yellow compounds to colorless derivatives

EXAMPLES

This invention can be further illustrated by the following examples of preferred embodiments thereof, although it will be understood that these examples are included merely for purposes of illustration and are not intended to limit the scope of the invention unless otherwise specifically indicated.

Comparative Example 1

Paraxylene was oxidized at 160° C. utilizing a Co, Mn, Br catalyst system to produce a crude terephthalic acid slurry having 30-35% solids. The crude terephthalic acid slurry was crystallized and purified using the process shown in FIG. 1 with the omission of Zone 180 and the crystallized product from the crystallization zone 120 was transferred directly to flash tank. The product was removed after filtration and drying and analyzed for 4-CBA, TMA, 2,6-DCF, percent transmittance and b*. The b* is one of the three-color attributes measured on a spectroscopic reflectance-based instrument. A Hunter Ultrascan XE instrument is typically the measuring device. Positive readings signify the degree of yellow (or absorbance of blue), while negative readings signify the degree of blue (or absorbance of yellow).

The concentration of 4-CBA, TMA, 2,6-DCF in the terephthalic acid were analyzed via liquid chromatography. To determine the percent transmittance, a 10% solution of terephthalic acid product in 2M KOH was measured using a UV visible spectrometer at 340 nm. The results are shown in Table 1.

Inventive Example 2

Example 1 was repeated except that the crystallized product from the crystallization zone 120 was fed to a solid liquid separation zone 180 comprising a rotary disk centrifuge at a temperature of 155° C. and the solvent wash was fed to the rotary disk centrifuge at a temperature of 145° C. The purified terephthalic acid product was collected and analyzed as in Example 1. The results are shown in Table 1.

TABLE 1

| Ex. # | 4-CBA[1] (ppm) | TMA[2] (ppm) | 2,6-DCF[3] (ppm) | % T[4] | b*[5] |
|---|---|---|---|---|---|
| 1 | 103 | 51 | 10 | 89 | 4.1 |
| 2 | 44 | 23 | 4 | 95 | 2.9 |

[1]4-CBA is 4-carboxybenzaldehyde
[2]TMA is trimellitic acid
[3]2,6-DCF is 2,6-dicarboxyfluorenone
[4]% T is % transmittance at 340 nm
[5]b* is a measure of yellow-blue color The results of Examples 1 and 2 clearly illustrate the significant purity improvements which are achieved when the solid liquid displacement zone of the present invention is used. The amount of impurities present in the purified terephthalic acid product produced by the process of the present invention decreased between about 50 and about 60%. The % transmittance of the purified terephthalic acid product has a direct influence on the color of the polyethylene terephthalate (PET) produced. Desirable PTA (purified terephthalic acid) is white (which is referred to as having low color). Higher % transmittance indicates less color in the PTA. The human eye can detect 0.5 differences in b*. Thus, the 1.2 difference between the non-hydrogenation process (Example 1) which displays a b* of greater than about 4, and the process of the present invention (Example 2) which shows a b* less than about 3 represents a very noticeable decrease in the yellowness of the terephthalic acid slurry. The degree of improvement in all the measured categories is particularly surprising given the simplicity of the centrifugation in the solid liquid separation zone 180. In the past, comparable purity levels have been achieved only by utilization of a hydrogenation plant which includes numerous steps and pieces of equipment, and significant capital investment.

The invention has been described in detail with particular reference to preferred embodiments thereof, but it will be understood that variations and modifications can be effected within the spirit and scope of the invention.

Inventive Example 3

Five staged oxidation experiments were conducted with samples taken directly from an oxidation reaction. The experiments were designed to demonstrate that crude terephthalic acid particles could be oxidized in a staged oxidation zone at temperatures as low as 160° C. The slurry contained 23% by weight crude terephthalic acid solids and the remainder was mother liquor from the oxidation reaction. The slurry was separated into liquid and solid fractions by solid liquid separation in order to facilitate batch digestion experiments. The liquid fraction was charged to a titanium autoclave. The headspace was purged with nitrogen and was subsequently pressurized to 180 psig with nitrogen. The autoclave was heated via hot oil in a jacket to the target digestion temperature. In these experiments, five separate experiments were conducted employing this procedure. The temperatures were 160° C., 170° C., 190° C., 200° C. When the target temperature had been reached, a charge of catalyst solution (in acetic acid solvent) was made to the autoclave that yielded concentrations of 500 ppm of cobalt, 600 ppm of bromine and 20 ppm of manganese in the vessel contents solution. The charge was made through a titanium blowcase connected to the autoclave. The pressure in the blowcase was maintained at 50 psig greater than the pressure in the autoclave. Subsequent to the catalyst charge, a solution containing 1 gram of peracetic acid was charged to the autoclave.

Finally, the solids originally separated from the oxidizer slurry sample were charged to the autoclave through the blowcase. As soon as the solids were charged to the autoclave, a 92/8 v/v % nitrogen/oxygen mixture was purged through the headspace at a rate of 230 sccm. As soon as the gas purge was switched on, a slurry sample was removed from the base of the autoclave. A part of the sample was separated into a liquid and solid fraction for analysis of both phases. Further samples were taken from the autoclave at regular intervals up to a maximum of 6 hours after oxygen supply was started to the autoclave. The samples were analyzed for the content of 4-carboxy benzaldehyde (4-CBA) and para-Toluic acid (pTA). The results of the analysis of the slurry samples are shown in table 1 for each experiment and the results of the analysis of the solid samples are shown in tables 2a&b.

From the results in tables 2a&b and 3a&b, it can be seen that a slurry concentration of less than 600 ppm 4-CBA and 250 ppm p-TA can be contained in the slurry after a oxidizing in a stage oxidation zone for a period of 6 hours. It can also be seen that the concentration of 4-CBA and p-TA can be reduced significantly in the solid phase after a oxidizing in a staged oxidation zone for a time of 6 hours at each temperature. The minimum concentration of 4-CBA and p-TA in the solid phase is inversely proportional to the demperature at which the sample was oxidized. Thus, the samples oxidized in a staged oxidation zone at 160° C. had a final 4-CBA concentration of 1126.2 ppm and the sample digested at 200° C. had a final 4-CBA concentration of 156.6 ppm.

We claim:

1. A process to produce a purified carboxylic acid composition said process comprising:
    (a) oxidizing an aromatic feedstock in a primary oxidation zone to form a crude carboxylic acid slurry;
    (b) oxidizing said crude carboxylic acid slurry in a staged oxidation zone to form a staged oxidation composition; wherein said staged oxidation zone comprises at least one staged oxidation reactor operated at a temperature of about 150° C. to about 280° C.;
    (c) crystallizing in a crystallization zone said staged oxidation composition to form a crystallized composition;
    (d) removing in a solid liquid displacement zone impurities from said crystallized composition to form said purified carboxylic acid slurry; wherein said impurities comprise 4-carboxybenzaldehyde, trimellitic acid, and 2,6-dicarboxyfluorenone; wherein said solid liquid displacement zone comprises a solid liquid separator that is operated at a temperature between 110° C. and 200° C.;
    (e) cooling said purified carboxylic acid slurry in a cooling zone to form a cooled purified carboxylic acid slurry; and
    (f) filtering and drying said cooled purified carboxylic acid slurry in a filtration and drying zone to produce said purified carboxylic acid composition.

2. The process according to claim 1 wherein said solid liquid displacement zone comprises a solid liquid separator that is operated at a temperature between about 110° C. to about 200° C.

3. The process according to claim 1 wherein said crude carboxylic acid slurry comprises terephthalic acid, catalyst, and acetic acid; wherein said catalyst comprises cobalt compounds, manganese compounds, and bromine compounds.

4. The process according to claim 1 wherein said solid liquid displacement zone comprises a solid liquid separator selected from the group consisting of a belt filter, a rotary vacuum filter and a rotary disk pack centrifuge.

5. The process according to claim 1 wherein said purified carboxylic acid slurry has a b* of less than about 3.5.

6. The process according to claim 1 further comprising the step of flash cooling said purified carboxylic acid slurry to form said cooled purified carboxylic acid slurry.

7. The process according to claim 1 wherein said staged oxidation reactor is operated at a temperature of about 190° C. to about 280° C.

8. A process to produce a purified carboxylic acid composition said process comprising:
    (a) oxidizing an aromatic feedstock in a primary oxidation zone to form a crude carboxylic acid slurry;
    (b) oxidizing said crude carboxylic acid slurry in a staged oxidation zone to form a staged oxidation composition; wherein said staged oxidation zone comprises at least one staged oxidation reactor operated at a temperature of about 150° C. to about 280° C.;
    (c) removing in a solid liquid displacement zone impurities from said staged oxidation composition to form a purified carboxylic acid slurry; wherein said impurities comprise 4-carboxybenzaldehyde, trimellitic acid, and 2,6-dicarboxyfluorenone; wherein said solid liquid displacement zone comprises a solid liquid separator that is operated at a temperature between 110° C. and 200° C.;
    (d) crystallizing in a crystallization zone said staged oxidation composition to form a crystallized composition;
    (e) cooling said crystallized composition in a cooling zone to form a cooled purified carboxylic acid slurry; and
    (f) filtering and drying said cooled purified carboxylic acid slurry in a filtration and drying zone to produce said purified carboxylic acid composition.

9. The process according to claim 8 wherein said crude carboxylic acid slurry comprises terephthalic acid, catalyst, and acetic acid; wherein said catalyst comprises cobalt compounds, manganese compounds, and bromine compounds.

10. The process according to claim 8 wherein said solid liquid displacement zone comprises a solid liquid separator selected from the group consisting of a belt filter, a rotary vacuum filter and a rotary disk pack centrifuge.

11. The process according to claim 8 wherein said purified carboxylic acid slurry is formed without a process for separating impurities from oxidation solvent or hydrogenation step.

12. The process according to claim 8 wherein said purified carboxylic acid slurry has a b* of less than about 3.5.

13. The process according to claim 8 further comprising the step of flash cooling said purified carboxylic acid slurry to form a cooled purified carboxylic acid slurry.

14. The process according to claim 8 wherein said staged oxidation reactor is operated at a temperature of about 190° C. to about 280° C.

15. A process to produce a purified carboxylic acid composition comprising:
    (a) oxidizing an aromatic feedstock in a primary oxidation zone to form a crude carboxylic acid slurry; wherein said oxidizing is conducted at a temperature between about 110° C. to about 200° C.;
    (b) oxidizing said crude carboxylic acid slurry in a staged oxidation zone to form a staged oxidation composition; wherein said oxidizing is conducted at a temperature between about 150° C. to about 280° C.; and wherein said oxidizing is at a higher temperature in said staged oxidation zone than in said primary oxidation zone;
    (c) crystallizing said staged oxidation composition in a crystallization zone to form a crystallized composition;
    (d) removing in a solid liquid displacement zone impurities from said crystallized composition to form said purified carboxylic acid slurry; wherein said solid liquid displacement zone comprises a solid liquid separator that is operated at a temperature between about 110° C. to about 200° C.; wherein said impurities comprise 4-carboxybenzaldehyde, trimellitic acid, and 2,6-dicarboxyfluorenone;

(b) cooling said purified carboxylic acid slurry in a cooling zone to form a cooled purified carboxylic acid slurry; and (c) filtering and drying said cooled purified carboxylic acid slurry in a filtration and drying zone to produce said purified carboxylic acid composition.

16. The process according to claim 15 further comprising the step of flash cooling said purified carboxylic acid slurry to form a cooled purified carboxylic acid slurry.

17. The process according to claim 1, 8 or 15 further comprising decolorizing in a reactor zone said purified carboxylic acid slurry or a carboxylic acid that has been esterified.

18. The process according to claim 15 wherein said staged oxidation zone comprises at least one staged oxidation reactor operated at a temperature of about 190° C. to about 280° C.

* * * * *